US009138599B2

(12) United States Patent
Cannell et al.

(10) Patent No.: US 9,138,599 B2
(45) Date of Patent: Sep. 22, 2015

(54) WAVING COMPOSITIONS

(75) Inventors: David W. Cannell, New Hope, PA (US); Christine Shin, Princeton, NJ (US); Karen M. Saiewitz, Belchertown, MA (US)

(73) Assignee: L'OREAL (FR)

( * ) Notice: Subject to any disclaimer, the term of this patent is extended or adjusted under 35 U.S.C. 154(b) by 48 days.

(21) Appl. No.: 13/142,974

(22) PCT Filed: Dec. 23, 2009

(86) PCT No.: PCT/US2009/006716
§ 371 (c)(1),
(2), (4) Date: Jul. 19, 2011

(87) PCT Pub. No.: WO2010/077338
PCT Pub. Date: Jul. 8, 2010

(65) Prior Publication Data
US 2011/0268682 A1    Nov. 3, 2011

Related U.S. Application Data

(60) Provisional application No. 61/204,090, filed on Dec. 31, 2008, provisional application No. 61/204,063, filed on Dec. 31, 2008.

(51) Int. Cl.
*A61K 8/46* (2006.01)
*A61Q 5/04* (2006.01)
*A61K 8/23* (2006.01)
*A61K 8/42* (2006.01)
*A61K 8/60* (2006.01)
*A61K 8/67* (2006.01)

(52) U.S. Cl.
CPC ... *A61Q 5/04* (2013.01); *A61K 8/23* (2013.01); *A61K 8/42* (2013.01); *A61K 8/60* (2013.01); *A61K 8/676* (2013.01); *A61K 2800/592* (2013.01)

(58) Field of Classification Search
CPC ............. A61Q 5/04; A61K 8/23; A61K 8/42; A61K 8/60; A61K 8/676; A61K 2800/592
USPC .................. 424/70.5, 71, 72; 132/7; 8/127.51
See application file for complete search history.

(56) References Cited

U.S. PATENT DOCUMENTS

| 2,623,002 | A | * | 12/1952 | Fricke | 514/474 |
| 3,966,903 | A | * | 6/1976 | Torii et al. | 424/70.4 |
| 4,158,704 | A | | 6/1979 | Baer et al. | |
| 4,214,596 | A | * | 7/1980 | Kaplan et al. | 132/204 |
| 4,228,810 | A | | 10/1980 | Moore et al. | |
| 4,243,659 | A | | 1/1981 | Balingit et al. | |
| 4,841,997 | A | | 6/1989 | Petrow | |
| 4,970,067 | A | | 11/1990 | Panandiker et al. | |
| 5,294,230 | A | | 3/1994 | Wu et al. | |
| 5,338,540 | A | | 8/1994 | Lee et al. | |
| 5,474,578 | A | | 12/1995 | Chan et al. | |
| 5,554,364 | A | | 9/1996 | Neill et al. | |
| 5,589,177 | A | | 12/1996 | Herb et al. | |
| 5,641,480 | A | * | 6/1997 | Vermeer | 424/70.24 |
| 5,656,280 | A | | 8/1997 | Herb et al. | |
| 5,942,216 | A | | 8/1999 | Herb et al. | |
| 6,022,547 | A | | 2/2000 | Herb et al. | |
| 6,855,312 | B1 | * | 2/2005 | Craig et al. | 424/74 |
| 2001/0008031 | A1 | | 7/2001 | Schultz et al. | |
| 2003/0125378 | A1 | | 7/2003 | Biatry et al. | |
| 2003/0143172 | A1 | * | 7/2003 | Ito et al. | 424/70.1 |
| 2005/0129652 | A1 | | 6/2005 | Keller et al. | |
| 2006/0272103 | A1 | * | 12/2006 | Barbarat | 8/405 |
| 2007/0166256 | A1 | | 7/2007 | Shiroyama et al. | |
| 2008/0044368 | A1 | | 2/2008 | Boumard et al. | |
| 2009/0317349 | A1 | | 12/2009 | Zaeska et al. | |

FOREIGN PATENT DOCUMENTS

| CN | 1267212 A | 9/2000 |
| CN | 1646084 A | 7/2005 |
| CN | 1698573 A | 11/2005 |
| DE | 19749164 A1 | 7/1998 |
| EP | 0190834 A2 | 8/1986 |
| JP | 59-051209 | 3/1984 |
| JP | 61-183213 | 8/1986 |
| JP | 64-066109 | 3/1989 |
| JP | 05-112432 B2 | 5/1993 |
| JP | 2000229819 A | 8/2000 |
| JP | 2003534389 A | 11/2003 |

OTHER PUBLICATIONS

International Search Report and Written Opinion, PCT/US09/06716, dated Feb. 25, 2010.
Chinese Office Action for Application No. 2009801534.22 dated Feb. 22, 2013.
Chinese Office Action for Application No. 200980153422.X dated Nov. 20, 2013.
Chinese Office Action for Application No. 200980153422.X dated Jul. 28, 2014.

* cited by examiner

*Primary Examiner* — Ernst V Arnold
*Assistant Examiner* — Hong Yu
(74) *Attorney, Agent, or Firm* — Lerner, David, Littenberg, Krumholz & Mentlik, LLP

(57) ABSTRACT

Disclosed are waving compositions for waving of keratinous fibers, such as hair, containing a) a bisulfite compound, b) a sulfate compound or urea, and c) a lactone or about 0.3% or greater, by weight, of ascorbic acid or a derivative thereof, based on the total weight of the composition and methods of waving keratinous fibers by applying such compositions to keratinous fibers. Also disclosed is a multi-unit cosmetic kit for treating a keratinous fiber containing a) a first unit containing a first composition containing a bisulfite compound and a sulfate compound or urea, and b) a second unit containing a second composition containing a lactone or ascorbic acid or a derivative thereof.

20 Claims, No Drawings

WAVING COMPOSITIONS

CROSS-REFERENCE TO RELATED APPLICATIONS

The present application is a national phase entry under 35 U.S.C. §371 of International Application No. PCT/US2009/006716, filed Dec. 23, 2009, published in English, which claims priority from U.S. Provisional Patent Application Nos. 61/204,090 and 61/204,063, both filed Dec. 31, 2008, all of which are incorporated herein by reference.

BACKGROUND OF THE INVENTION

Compositions for waving of hair contain a reducing agent for breaking the disulfide bonds in hair, thereby allowing the hair to be permanently reshaped. U.S. Pat. No. 4,158,704 teaches methods for waving of hair using compositions containing thioglycolate compounds as the reducing agents. Thioglycolate compositions produce waving of hair that typically lasts about 3 to 4 months. However, mercaptan or thioglycolates produce a strong unpleasant odor.

U.S. Pat. No. 5,338,540 teaches hair waving compositions containing a sulfite and/or bisulfite reducing system, urea, and a cationic polyquaternary resin, which purportedly yield a hair waving or straightening effect equivalent to thioglycolate compositions without the unpleasant odors associated with thioglycolate. Bisulfite compounds produce a waving of hair that is shorter in duration, i.e., lasting from about 1 to 2 months. Bisulfites, however, are known to strip color from artificially colored hair.

SUMMARY OF THE INVENTION

A first aspect of the present invention is directed to a waving composition for waving of keratinous fibers containing a) a bisulfite compound, b) a sulfate compound or urea, and c) a lactone or about 0.3% or greater, by weight, of ascorbic acid or a derivative thereof, based on the total weight of the composition. In certain embodiments, the compositions do not contain a thioglycolate, e.g., as an additional reducing agent.

A second aspect of the present invention is directed to a method for waving of keratinous fibers by applying to a keratinous fiber a waving composition containing a) a bisulfite compound, b) a sulfate compound or urea, and c) a lactone or about 0.3% or greater, by weight, of ascorbic acid or a derivative thereof, based on the total weight of the composition. In certain embodiments, the methods do not include applying a thioglycolate, e.g., as an additional reducing agent, to the keratinous fibers.

A third aspect of the present invention is directed to a multi-unit cosmetic kit for treating a keratinous fiber containing a) a first unit containing a first composition containing a bisulfite compound and a sulfate compound or urea, and b) a second unit containing a second composition containing a lactone or ascorbic acid or a derivative thereof.

Underlying the present invention is the discovery that the combination of a bisulfite compound, a sulfate compound or urea, and a lactone or ascorbic acid or a derivative thereof provides a waving composition having improved properties with regard to curl, wear, and color fading. The waving compositions of the present invention may be applied to keratinous fibers to produce a tight wave that may last for about 1 to about 2 months with relatively little color fading. As illustrated in the working examples herein, embodiment(s) of the present invention exhibited unexpectedly less color fading compared to a commercial product that contains thioglycolates and compared to compositions containing a bisulfite compound, a sulfate compound or urea, but not containing any lactone or ascorbic acid or a derivative thereof.

DETAILED DESCRIPTION

In the waving compositions of the present invention, the bisulfite compound acts as a reducing agent that breaks the disulfide bonds of the cysteine of the keratinous fiber. The bisulfite compounds useful to make the present invention are generally provided in the form of a cosmetically acceptable salt. In an embodiment of the present invention, the bisulfite compound used to prepare the compositions is generally provided as an ammonium, alkanol amine, alkali metal, or alkali earth metal bisulfite salt, such as, ammonium bisulfite, monoethanolamine bisulfite, sodium bisulfite, potassium bisulfite, or calcium bisulfite.

The bisulfite compound, e.g., ammonium bisulfite, may be present in the compositions of the present invention in an amount that generally ranges from about 4% to about 20%, and in some embodiments, from about 6% to about 18%, and in yet other embodiments about 6%, about 8%, or about 10%, wherein all percentages are based on the total weight of the cosmetic composition. In certain embodiments, the amount of the bisulfite compound is about 10%, based on the total weight of the composition.

The sulfate compounds used in the present invention may also be provided in the form of a cosmetically acceptable salt, e.g., sulfate salts of weak bases. Suitable examples include ammonium sulfate, monoethanolamine lauryl sulfate, monoethanolamine laureth sulfate and triethanolamine sulfate.

The sulfate compound may be present in the compositions of the present invention in an amount that generally ranges from about 0.1% to about 20%, and in some embodiments, from about 0.2% to about 5%, and in yet other embodiments from about 0.4% to about 4%, wherein all percentages are based on the total weight of the cosmetic composition. In a certain embodiments, the amount of the sulfate compound is from about 1.0% to about 2.0%, such as about 1.1%, 1.2%, 1.3%, 1.4%, 1.5%, 1.6%, 1.7%, 1.8%, or 1.9% based on the total weight of the composition.

In some embodiments of the present invention, urea is present (with or without the sulfate compound). As used herein, "urea" is a compound having the formula $(NH_2)_2CO$; it is also known as carbamide. In the waving compositions of the present invention, urea acts to swell the shaft of the keratinous fiber to facilitate penetration of the bisulfite compound into the keratinous fiber. Urea may be present in the compositions of the present invention in an amount that generally ranges from about 0.1% to about 20%, and in some embodiments, from about 0.2% to about 10%, and in yet other embodiments from about 0.4% to about 5%, wherein all percentages are based on the total weight of the cosmetic composition. In a certain embodiments, the amount of urea is from about 2% to about 3%, such as, about 2.1%, 2.2%, 2.3%, 2.4%, 2.5%, 2.6%, 2.7%, 2.8%, or 2.9%, of the total weight of the composition.

As used herein, the term "lactone" refers to a compound containing a cyclic ester, except ascorbic acid. Representative examples of lactones include δ-gluconolactone, β-propiolactone, γ-butrylolactone, and ε-caprolactone.

The lactone may be present in the compositions of the present invention in an amount that generally ranges from about 0.1% to about 10%, and in some embodiments, about 0.2% to about 8%, and in yet other embodiments about 0.5% to about 4%, wherein all percentages are based on the total weight of the cosmetic composition. In some embodiments, the lactone is δ-gluconolactone and is present in an amount of about 4% of the total weight of the composition.

Ascorbic acid, i.e., vitamin C, is a water-soluble vitamin. Derivatives of ascorbic acid refer to compounds in which ascorbic acid has been chemically modified, for example, to increase stability or to increase or decrease water or fat solubility. Representative examples of ascorbic acid derivatives include, for example, its cosmetically acceptable esters and salts. See, e.g., U.S. Patent Application Publication 2003/0125378. Specific examples that may be suitable for use in the present invention include magnesium ascorbyl phosphate and ascorbyl glucoside.

The ascorbic acid or a derivative thereof may be present in the compositions of the present invention in an amount of about 0.3% or greater, by weight, based on the total weight of the composition. In certain embodiments, ascorbic acid or a derivative thereof is present in the compositions in an amount that generally ranges from about 0.3% (e.g., 0.3% or slightly lower but as explained in working examples herein, not including 0.1%) to about 1, 2, 3, 4, 5, 6, 7, 8, 9, or 10%, or even higher, and including subranges therein, wherein all percentages are based on the total weight of the cosmetic composition.

In certain embodiments, the compounds of the present invention further contain a silicone compound. In an embodiment of the present invention, the silicone compound is an aminosilicone, such as amodimethicone. The silicone compound may be present in the compositions of the present invention in an amount that generally ranges from about 0.1% to about 5%, and in some embodiments, from about 0.2% to about 4%, and in yet other embodiments about 0.5% to about 2%, wherein all percentages are based on the total weight of the cosmetic composition.

The exact nature of the composition is not critical. For example, depending in part upon the amount of water that may be present, the waving composition may be in the form of an aqueous solution, dispersion, emulsion, or suspension. Thus, in certain embodiments, water is present in an amount of from about 0.1% to about 99%, in other embodiments from about 50% to about 98%, and in yet other embodiments from about 50% to about 75%, wherein all percentages are based on the total weight of the cosmetic composition.

The waving compositions of the present invention may contain a surfactant. Surfactants typically employed in the waving compositions of the present invention include amphoteric/zwitterionic surfactants, such as betaines, nonionic surfactants, anionic surfactants, and cationic surfactants. Suitable amphoteric surfactants include, for example, lauryl betaine, lauroamphoglycinate, lauroamphopropylsulfonate, lauroamphopropionate, lauroampho-carboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, and cocoamphopropylsulfonate.

Representative examples of suitable nonionic surfactants include, fatty acid esters and alkoxylated, particularly ethoxylated, fatty acid esters of polyhydric alcohols such as glycerols and sorbitol, for example, polyoxyethylene monolaurate, polyoxyethylene monooleate, polyoxyethylene monostearate, sorbitan monolaurate, sorbitan trioleate, generally with a degree of ethoxylation of from about 20 to about 85; mono- and di-alkanolamides, such as the N-acyl derivatives of mono- and di-ethanol amines, and polyethoxylated monoalkanolamides; amine oxides, such as cocoamidopropyl dimethylamine oxides, coco bis-2-hydroxyethyl amine oxides and lauryl dimmethylamine oxide; ethoxylated alkanolamides; ethoxylated oils and fats such as ethoxylated lanolins; and ethoxylated alkylphenols, such as Nonoxynol.

Suitable anionic surfactants include, for example, the following: the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about $C_{12}$ to $C_{18}$ alkyl or alkenyl groups. Particular examples include the salts of lauryl sulfates and lauryl ether sulfates the latter having an average level of ethoxylation of 1-3.

Suitable cationic surfactants include, for example, quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Surfactants are typically present in compositions of the present invention in amounts ranging from about 0.1% to about 5% by weight, and in some other embodiments from about 0.5% to about 3% by weight, relative to the total weight of the composition.

The waving compositions of the present invention may contain a chelating agent, such as amines, carboxylic acids, phosphonic acids, and polyphosphoric acids. Suitable examples of chelating agents include pentasodium penteate, edetic acid, glutamic tetraacetic acid, asparaginic tetraacetic acid, propyl diamine tetraacetic acid and metal salts of such acids.

Chelating agents are generally present in amounts less than about 2% by weight, and in some other embodiments less than about 1% by weight, relative to the total weight of the composition.

The waving compositions of the present invention may contain a swelling agent or penetration enhancer. Suitable swelling agents or penetration enhancers include lower alcohols and polyols, such as $C_1$ to $C_4$ alcohols and polyols. Representative examples of swelling agents or penetration enhancers include ethanol, propanol, isopropanol, 1,2-propylene glycol, 1,3-butanediol, glycerol, ethylcarbitol, benzyl alcohol, benzyloxyethanol, urea and 2-methylpyrrolidone.

Swelling agents or penetration enhancers are generally present in amounts ranging from about 0.1% to about 10% by weight, and in some other embodiments from about 1% to about 5% by weight, relative to the total weight of the composition.

The waving compositions of the present invention may contain a pH adjuster. Representative examples of pH adjusters include organic acids such as citric acid, malic acid, lactic acid, succinic acid and oxalic acid, sodium salts of the acids, and alkaline agents such as ammonia, monoethanolamine, diethanolamine, triethanolamine, sodium hydroxide, potassium hydroxide, sodium carbonate, sodium hydrogencarbonate, potassium carbonate and potassium hydrogencarbonate.

The pH of the waving compositions of the present invention generally ranges from moderately acidic to moderately alkaline. In an embodiment of the present invention, the pH of the waving composition is in the range of about 5 to about 9. In other embodiments the pH is about 7 to about 8. In some embodiments, the pH of the waving composition is about 7.

The waving compositions may further contain at least one further cosmetically acceptable ingredient suitable for hair care. Examples of such ingredients are familiar to one of skill in the art and include solvents, structuring agents such as waxes and polymers, hydrophobic (lipophilic) and hydrophilic thickeners or gelling agents, skin conditioning agents, sunscreen agents (e.g., octocrylene, octinoxate, avobenzone), preservatives (e.g., sodium citrate, phenoxyethanol, parabens and mixtures thereof), cosmetically active agents and dermatological active agents such as, for example, hydrolyzed peptides, farnesol, bisabolol, phytantriol, aesthetic agents such as essential oils, fragrances, skin sensates, opacifiers, aromatic compounds (e.g., clove oil, menthol, camphor, eucalyptus oil, and eugenol), foam enhancers, botanical extracts, and anti-inflammatory agents.

In the method for waving of a keratinous fiber of the present invention, the waving composition of the present invention is applied to keratinous fibers (natural or synthetic), such as hair, to maintain a desired shape. Typically, water is applied to the keratinous fibers and the wet fibers are styled into a desired shape, e.g., wrapped around a rod. The waving composition of the present invention is then applied to the styled keratinous fibers, rinsed with water, and dried.

The compositions of the present invention may be applied by hand. Alternatively, or in conjunction therewith, they may be applied via an applicator such as a sponge, cotton, brush or a puff of a natural or synthetic material. In addition, the applicator may be attached to a container, the container serving as a reservoir for the waving composition.

The keratinous fibers are in contact with the waving composition for a period of time sufficient to allow the waving composition to break sufficient disulfide bonds in the keratinous fibers to allow for waving. In embodiments of the present invention, the keratinous fibers are in contact with the waving composition for about 10 minutes to about 60 minutes, in other embodiments for about 20 minutes to about 40 minutes, and in yet other embodiments for about 25 minutes.

In an embodiment of the present invention, a neutralizer composition is applied to the hair after the waving composition has been applied to keratinous fibers. Generally, the neutralizer composition is applied to the keratinous fibers after the waving composition has been rinsed from the keratinous fibers. The neutralizer is then rinsed from the keratinous fibers with water and the fibers are dried to produce the desired shape.

The neutralizer composition of the present invention contains an oxidizing agent. When applied after the waving composition, the neutralizer composition reforms the disulfide bonds in the keratinous fiber broken by the reducing agent in the waving composition. This fixes the hair in the desired shape for a longer period than if the neutralizer composition were not used. Suitable oxidizing agents include peroxides, bromates, and perborates. Specific examples include hydrogen peroxide, potassium bromate, sodium bromate, and sodium perborate. In an embodiment of the present invention, the neutralizer composition is acidic and has a pH between about 2 and about 5, e.g., about 3.

The neutralizer composition may also contain a pH adjuster such as phosphoric acid, a hair conditioning agent, such as a quaternary ammonium salt, e.g., dicetyldimonium chloride (commercially available from EVONIK Goldschmidt GmbH (Westfalen, Germany) as VARISOFT 432 CG®), or a siloxane, e.g., amodimethicone, a surfactant, such as a quaternary ammonium salt, e.g., cetrimonium chloride, or a polyethylene glycol ether of an alcohol, e.g., trideceth-12, and water. A mixture of 31% amodimethicone, 2.2% cetrimonium chloride, and 1.9% trideceth-12 is commercially available from Dow Corning (Midland, Mich.) under the trade name 949 CATIONIC EMULSION®.

The neutralizer composition may further contain at least one additional ingredient suitable for hair care. Examples of such ingredients are familiar to one of skill in the art and include chelating agents, swelling agents or penetration enhancers, solvents, emulsifiers, structuring agents such as waxes and polymers, hydrophobic (lipophilic) and hydrophilic thickeners or gelling agents, skin conditioning agents, sunscreen agents (e.g., octocrylene, octinoxate, avobenzone), preservatives (e.g., sodium citrate, phenoxyethanol, parabens and mixtures thereof), cosmetically active agents and dermatological active agents such as, for example, hydrolyzed peptides, farnesol, bisabolol, phytantriol, aesthetic agents such as essential oils, fragrances, skin sensates, opacifiers, aromatic compounds (e.g., clove oil, menthol, camphor, eucalyptus oil, and eugenol), foam enhancers, botanical extracts, and anti-inflammatory agents.

The keratinous fibers are in contact with the neutralizer composition for a period of time sufficient to allow the neutralizer composition to reform sufficient disulfide bonds in the keratinous fibers to allow for longer lasting waving. In an embodiment of the present invention, the keratinous fibers are in contact with the neutralizer composition for about 1 minute to about 20 minutes; in another embodiment for about 2 minutes to about 10 minutes, and in yet another embodiment for about 5 minutes.

The multi-unit cosmetic kits of the present invention contain a first unit containing a bisulfite compound and urea or a sulfate compound and a second unit containing a lactone or ascorbic acid or a derivative thereof. In use, the lactone or ascorbic acid or a derivative thereof is added to the bisulfite and urea or sulfate composition to form a waving composition of the present invention prior to its application to a keratinous fiber. In an embodiment, the lactone or ascorbic acid or a derivative thereof is added to the bisulfite and urea or sulfate composition immediately prior to application of the waving composition to the keratinous fiber. In an embodiment of the present invention, the bisulfite compound and urea or the sulfate compound in the first unit are present in an aqueous composition, and the lactone or ascorbic acid or a derivative thereof is provided in a dry form, such as a tablet, powder, or granule. The dry lactone or ascorbic acid or a derivative thereof is added to the aqueous composition and dissolved therein to form a waving composition of the present invention, which may then be used in accordance with the method of the present invention. In some embodiments, the cosmetic kit further includes a third unit containing a neutralizer composition.

The following examples are intended to further illustrate the present invention. They are not intended to limit the invention in any way. Unless otherwise indicated, all parts are by weight.

EXAMPLES

Example 1

Inventive Compositions

Waving compositions of the present invention were made as follows:

Waving Composition Formula 1A:

| INGREDIENT | AMOUNT (Wt %) |
|---|---|
| δ-Gluconolactone | 4 |
| Ammonium Bisulfite | 10 |
| Pentasodium Pentetate | 0.16 |
| Ammonium Sulfate | 1.2 |
| Cocamidopropyl betaine | 1.75 |
| Isopropanol | 2.0 |
| Monoethanolamine | Adjust pH to 7.0 |
| Deionized Water | QS to 100 |

Waving Composition Formula 1B:

| INGREDIENT | AMOUNT (Wt %) |
|---|---|
| δ-Gluconolactone | 4 |
| Ammonium Bisulfite | 10 |
| Pentasodium Pentetate | 0.16 |
| Urea | 2.3 |
| Cocamidopropyl betaine | 1.75 |
| Isopropanol | 2.0 |
| Monoethanolamine | Adjust pH to 7.0 |
| Deionized Water | QS to 100 |

Using Waving Composition Formula 1A or 1B, deionized water was heated in a tank to 80° C. and the δ-gluconolactone was added. When the δ-gluconolactone acid was completely dissolved and the mixture became clear and uniformly mixed, the remaining ingredients were added in the order listed while mixing until uniform between each addition. Monoethanolamine ("MEA") was added to adjust solution to pH 7.0. The solution was then QS to 100% with deionized water.

Example 2

Comparative Compositions

Comparative compositions lacking the lactone were made as follows:
Comparative Composition Formula 2A:

| INGREDIENT | AMOUNT (Wt %) |
|---|---|
| Ammonium Bisulfite | 10 |
| Pentasodium Pentetate | 0.16 |
| Ammonium Sulfate | 1.2 |
| Cocamidopropyl betaine | 1.75 |
| Isopropanol | 2.0 |
| Monoethanolamine | Adjust pH to 7.0 |
| Deionized Water | QS to 100 |

Comparative Composition Formula 2B:

| INGREDIENT | AMOUNT (Wt %) |
|---|---|
| Ammonium Bisulfite | 10 |
| Pentasodium Pentetate | 0.16 |
| Urea | 2.3 |
| Cocamidopropyl betaine | 1.75 |
| Isopropanol | 2.0 |
| Monoethanolamine | Adjust pH to 7.0 |
| Deionized Water | QS to 100 |

Using Comparative Composition Formula 2A or 2B, deionized water was loaded into a tank and the ingredients were added in the order listed. MEA was used to adjust pH to 7.0. The solution was then QS to 100% with deionized water.

Example 3

The inventive waving compositions of Example 1, the comparative compositions of Example 2, and a commercially available waving composition containing ammonium thioglycolate were each evaluated and compared using 2 colored hair swatches as follows:

Method for Coloring Hair Swatches:

Artificially colored hair swatches for testing were produced using the following method. Natural white hair swatches were obtained, measuring 1 cm wide, 14 cm long, and weighing 2.8 g, were dyed with Color Fusion™ 5VR (Redken (New York, N.Y.)) with Pro-oxide 20vol developer at 1:1 ratio, and processed for 30 minutes. Each swatch was then shampooed for 35 seconds using Redken Cleaning Cream and rinsed well for 25 seconds with water at 40° C.

Method for Treating Hair Swatches and Measuring Color Change:

The colored hair swatches were air-dried and measured for an initial color reading using Konica Minolta Spectrophotometer with SpectraMagic™ software to measure for L*a*b* values. This L*a*b value was the initial value that will be compared to a value obtained for each swatch after treatment.

Two strips of the artificially colored hair swatches were placed on a weight boat and enough of the appropriate waving or comparative formula was added to the weight boat to immerse the swatches. Swatches were immersed for 25 minutes and rinsed with water at 40° C. for 3 minutes. Swatches were then towel-blotted and placed on another weigh boat. Enough of the hydrogen-peroxide based neutralizer, described below, was added the weight boat to immerse the hair swatches. The swatches were immersed in the neutralizer for 5 minutes.

A hydrogen peroxide neutralizer was produced having the following formula:

| INGREDIENT | AMOUNT (Wt %) |
|---|---|
| Deionized water | QS to 100 |
| Hydrogen Peroxide | 1.6-2.40% |
| Varisoft 432 CG ® | 0.50% |
| Dow Corning 949 Cationic Emulsion ® | 2.00% |
| Phosphoric Acid | Adjust pH to 3.0 |

Deionized water was added to a tank. The ingredients were then added to the tank in the order listed above. Phosphoric acid was added to adjust the pH of the solution to 3.0. The solution was then QS to 100% with deionized water.

Swatches were then rinsed with 40° C. water for 3 minutes. The swatches were air-dried and measured for color readings using Konica Minolta® Spectrophotometer to measure for L*a*b* values. According to this system, the overall color change from the initial to the final (after-treatment) color reading, ΔE, was calculated from the ΔL, Δa, and Δb values. For purposes of the present invention, a difference in ÿE values of at least 3 is considered as a statistically significant difference in color retention.

| Formula | Average ΔE |
|---|---|
| Waving Composition Formula 1A | 12.3 |
| Waving Composition Formula 1B | 15.4 |
| Comparative Composition 2A | 16.2 |
| Comparative Composition 2B | 22.0 |
| Thioglycolate Waving Composition | 30.7 |

The results show that swatches treated with the inventive waving compositions containing a lactone retained more color compared to swatches treated with the comparative compositions without the lactone, and compared to a commercial product containing thioglycolate.

Method for Preparing and Treating Colored Test Curl Swatches ("Curl Samples") to Evaluate Curl:

Using the artificially colored hair swatches, curl samples were made by gluing 20 strands of artificially colored hair that were 4 7/16 inches in length. Five (5) curl samples wrapped around a curing rod were placed on a weight boat and immersed in the appropriate waving or comparative composition. The curl samples were processed for 25 minutes and rinsed with 40° C. water for 3 minutes.

The curl samples were then towel-blotted, placed in a weight boat, and neutralized by immersion in the hydrogen peroxide neutralizer for 5 minutes. The curl samples were then rinsed with 40° C. water for 3 minutes. The curl samples were taken out of the rods and air-dried.

The length of each of the curled swatches was measured and an average taken.

| Formula | Average Curl Length (cm) |
| --- | --- |
| Waving Composition Formula 1A | 8.24 |
| Waving Composition Formula 1B | 7.78 |
| Comparative Composition 2A | 7.34 |
| Comparative Composition 2B | 7.68 |

The results show that curl samples treated with the inventive waving compositions containing a lactone had comparable curl length compared to comparative compositions without the lactone.

Example 4

The inventive waving compositions of Example 1 and the comparative compositions of Example 2 were evaluated and compared for color change using 6 colored hair swatches as described in Example 3. The results are reported below.

| Formula | Average ΔE |
| --- | --- |
| Waving Composition Formula 1A | 17.54 |
| Waving Composition Formula 1B | 21.62 |
| Comparative Composition 2A | 19.02 |
| Comparative Composition 2B | 25.03 |

The results show that swatches treated with the inventive waving compositions containing a lactone retained significantly more color compared to swatches treated with the comparative compositions without the lactone.

Example 5

Waving compositions of the present invention with 6% and 8% ammonium bisulfite are made having the following formulas using the same procedure described in Example 1.

| INGREDIENT | AMOUNT (Wt %) | | | |
| --- | --- | --- | --- | --- |
| | Formula 5A | Formula 5B | Formula 5C | Formula 5D |
| δ-Gluconolactone | 4 | 4 | 4 | 4 |
| Ammonium Bisulfite | 6 | 8 | 6 | 8 |
| Pentasodium Pentetate | 0.16 | 0.16 | 0.16 | 0.16 |
| Ammonium Sulfate | 1.2 | 1.2 | — | — |
| Urea | — | — | 2.3 | 2.3 |
| Cocamidopropyl betaine | 1.75 | 1.75 | 1.75 | 1.75 |
| Isopropanol | 2.0 | 2.0 | 2.0 | 2.0 |
| Monoethanolamine | Adjust pH to 7.0 | Adjust pH to 7.0 | Adjust pH to 7.0 | Adjust pH to 7.0 |
| Deionized Water | QS to 100 | QS to 100 | QS to 100 | QS to 100 |

Example 6

Waving compositions of the present invention with 0.5%, 1.0%, or 2.0% δ-gluconolactone are made having the following formulas using the same procedure described in Example 1.

| INGREDIENT | AMOUNT (Wt %) | | | | | |
| --- | --- | --- | --- | --- | --- | --- |
| | Formula 6A | Formula 6B | Formula 6C | Formula 6D | Formula 6E | Formula 6F |
| δ-Gluconolactone | 0.5 | 1.0 | 2.0 | 0.5 | 1.0 | 2.0 |
| Ammonium Bisulfite | 10.0 | 10.0 | 10.0 | 10.0 | 10.0 | 10.0 |
| Pentasodium Pentetate | 0.16 | 0.16 | 0.16 | 0.16 | 0.16 | 0.16 |
| Ammonium Sulfate | 1.2 | 1.2 | 1.2 | — | — | — |
| Urea | — | — | — | 2.3 | 2.3 | 2.3 |
| Cocamidopropyl betaine | 1.75 | 1.75 | 1.75 | 1.75 | 1.75 | 1.75 |
| Isopropanol | 2.0 | 2.0 | 2.0 | 2.0 | 2.0 | 2.0 |
| Monoethanolamine | Adjust pH to 7.0 | Adjust pH to 7.0 | Adjust pH to 7.0 | Adjust pH to 7.0 | Adjust pH to 7.0 | Adjust pH to 7.0 |
| Deionized Water | QS to 100 | QS to 100 | QS to 100 | QS to 100 | QS to 100 | QS to 100 |

Example 7

Waving compositions of the present invention with 0.5%, 1.0%, or 2.0% amodimethicone are made having the following formulas using the same procedure described in Example 1.

| INGREDIENT | AMOUNT (Wt %) | | | | | |
|---|---|---|---|---|---|---|
| | Formula 7A | Formula 7B | Formula 7C | Formula 7D | Formula 7E | Formula 7F |
| δ-Gluconolactone | 4.0 | 4.0 | 4.0 | 4.0 | 4.0 | 4.0 |
| Ammonium Bisulfite | 10.0 | 10.0 | 10.0 | 10.0 | 10.0 | 10.0 |
| Pentasodium Pentetate | 0.16 | 0.16 | 0.16 | 0.16 | 0.16 | 0.16 |
| Ammonium Sulfate | 1.2 | 1.2 | 1.2 | — | — | — |
| Urea | — | — | — | 2.3 | 2.3 | 2.3 |
| Cocamidopropyl betaine | 1.75 | 1.75 | 1.75 | 1.75 | 1.75 | 1.75 |
| Isopropanol | 2.0 | 2.0 | 2.0 | 2.0 | 2.0 | 2.0 |
| Amodimethicone | 0.5 | 1.0 | 2.0 | 0.5 | 1.0 | 2.0 |
| Monoethanolamine | Adjust pH to 7.0 | Adjust pH to 7.0 | Adjust pH to 7.0 | Adjust pH to 7.0 | Adjust pH to 7.0 | Adjust pH to 7.0 |
| Deionized Water | QS to 100 | QS to 100 | QS to 100 | QS to 100 | QS to 100 | QS to 100 |

The amodimethicone is provided as part of the composition Wacker-Belsil ADM Log 1® (Wacker Chemie AG (Munich, Germany)), which consists of amodimethicone at 15%, Glycerin at 3.5%, Trideceth-5 at 6% and Trideceth-10 at 1.5%.

Example 8

Inventive Compositions

Waving compositions of the present invention were made as follows:

| INGREDIENT | AMOUNT (Wt %) | | | | | |
|---|---|---|---|---|---|---|
| | Formula 8A | Formula 8B | Formula 8C | Formula 8D | Formula 8E | Formula 8F |
| Ascorbic Acid | 4.0 | — | — | 4.0 | — | — |
| Magnesium Ascorbyl Phosphate | — | 4.0 | — | — | 4.0 | — |
| Ascorbyl Glucoside | — | — | 4.0 | — | — | 4.0 |
| Ammonium Bisulfite | 10.0 | 10.0 | 10.0 | 10.0 | 10.0 | 10.0 |
| Pentasodium Pentetate | 0.16 | 0.16 | 0.16 | 0.16 | 0.16 | 0.16 |
| Ammonium Sulfate | 1.2 | 1.2 | 1.2 | — | — | — |
| Urea | — | — | — | 2.3 | 2.3 | 2.3 |
| Cocamidopropyl betaine | 1.75 | 1.75 | 1.75 | 1.75 | 1.75 | 1.75 |
| Isopropanol | 2.0 | 2.0 | 2.0 | 2.0 | 2.0 | 2.0 |
| Monoethanolamine | Adjust pH to 7.0 | Adjust pH to 7.0 | Adjust pH to 7.0 | Adjust pH to 7.0 | Adjust pH to 7.0 | Adjust pH to 7.0 |
| Deionized Water | QS to 100 | QS to 100 | QS to 100 | QS to 100 | QS to 100 | QS to 100 |

Using one of the Waving Composition Formulas 8A-8F, deionized water was heated in a tank to 80° C. and the ascorbic acid, magnesium ascorbyl phosphate, or ascorbyl glucoside was added. When the ascorbic acid, magnesium ascorbyl phosphate, or ascorbyl glucoside was completely dissolved and the mixture became clear and uniformly mixed, the remaining ingredients were added in the order listed while mixing until uniform between each addition. Monoethanolamine ("MEA") was added to adjust solution to pH 7.0. The solution was then QS to 100% with deionized water.

Example 9

Comparative Compositions

Comparative compositions lacking the ascorbic acid or derivative thereof were made as follows:
Comparative Composition Formula 9A:

| INGREDIENT | AMOUNT (Wt %) |
|---|---|
| Ammonium Bisulfite | 10 |
| Pentasodium Pentetate | 0.16 |

-continued

| INGREDIENT | AMOUNT (Wt %) |
|---|---|
| Ammonium Sulfate | 1.2 |
| Cocamidopropyl betaine | 1.75 |

-continued

| INGREDIENT | AMOUNT (Wt %) |
|---|---|
| Isopropanol | 2.0 |
| Monoethanolamine | Adjust pH to 7.0 |
| Deionized Water | QS to 100 |

Comparative Composition Formula 9B:

| INGREDIENT | AMOUNT (Wt %) |
|---|---|
| Ammonium Bisulfite | 10 |
| Pentasodium Pentetate | 0.16 |
| Urea | 2.3 |
| Cocamidopropyl betaine | 1.75 |
| Isopropanol | 2.0 |
| Monoethanolamine | Adjust pH to 7.0 |
| Deionized Water | QS to 100 |

Using Comparative Composition Formula 9A or 9B, deionized water was loaded into a tank and the ingredients were added in the order listed. MEA was used to adjust pH to 7.0. The solution was then QS to 100% with deionized water.

Example 10

The inventive waving compositions of Example 8, the comparative compositions of Example 9, and a commercially available waving composition containing ammonium thioglycolate were each evaluated and compared using 2 colored hair swatches as follows:

Method for Coloring Hair Swatches:

Artificially colored hair swatches for testing were produced using the following method. Natural white hair swatches were obtained, measuring 1 cm wide, 14 cm long, and weighing 2.8 g, were dyed with Color Fusion™ 5VR (Redken, (New York, N.Y.)) with Pro-oxide 20vol developer at 1:1 ratio, and processed for 30 minutes. Each swatch was then shampooed for 35 seconds using Redken Cleaning Cream™ and rinsed well for 25 seconds with water at 40° C.

Method for Treating Hair Swatches and Measuring Color Change:

The colored hair swatches were air-dried and measured for an initial color reading using Konica Minolta Spectrophotometer with SpectraMagic™ software to measure for $L^*a^*b^*$ values. This $L^*a^*b$ value was the initial value that will be compared to a value obtained for each swatch after treatment.

Two strips of the artificially colored hair swatches were placed on a weight boat and enough of the appropriate waving or comparative formula was added to the weight boat to immerse the swatches. Swatches were immersed for 25 minutes and rinsed with water at 40° C. for 3 minutes. Swatches were then towel-blotted and placed on another weigh boat. Enough of the hydrogen-peroxide based neutralizer, described below, was added the weight boat to immerse the hair swatches. The swatches were immersed in the neutralizer for 5 minutes.

A hydrogen peroxide neutralizer was produced having the following formula:

| INGREDIENT | AMOUNT (Wt %) |
|---|---|
| Deionized water | QS to 100 |
| Hydrogen Peroxide | 1.6-2.40% |
| Varisoft 432 CG ® | 0.50% |

| INGREDIENT | AMOUNT (Wt %) |
|---|---|
| Dow Corning 949 Cationic Emulsion ® | 2.00% |
| Phosphoric Acid | Adjust pH to 3.0 |

Swatches were then rinsed with 40° C. water for 3 minutes. The swatches were air-dried and measured for color readings using Konica Minolta® Spectrophotometer to measure for $L^*a^*b^*$ values. According to this system, the overall color change from the initial to the final (after-treatment) color reading, $\Delta E$, was calculated from the $\Delta L$, $\Delta a$, and $\Delta b$ values. For purposes of the present invention, a difference in $\Delta E$ values of at least 3 is considered as a statistically significant difference in color retention.

| Formula | Average $\Delta E$ |
|---|---|
| Waving Composition Formula 8A | 12.3 |
| Waving Composition Formula 8B | 12.6 |
| Waving Composition Formula 8C | 12.7 |
| Waving Composition Formula 8D | 14.4 |
| Waving Composition Formula 8E | 19.1 |
| Waving Composition Formula 8F | 12.2 |
| Comparative Composition 9A | 16.2 |
| Comparative Composition 9B | 22.0 |
| Thioglycolate Waving Composition | 30.7 |

The results show that swatches treated with the inventive waving compositions containing ascorbic acid or a derivative thereof retained more color compared to swatches treated with the comparative compositions without ascorbic acid or a derivative thereof, or compared to a commercial product containing thioglycolate.

Method for Preparing and Treating Colored Test Curl Swatches ("Curl Samples") to Evaluate Curl:

Using the artificially colored hair swatches, curl samples were made by gluing 20 strands of artificially colored hair that were 4 7/16 inches in length. 5 curl samples wrapped around a curing rod were placed on a weight boat and immersed in the appropriate waving or comparative composition. The curl samples were processed for 25 minutes and rinsed with 40° C. water for 3 minutes.

The curl samples were then towel-blotted, placed in a weight boat, and neutralized by immersion in the hydrogen peroxide neutralizer for 5 minutes. The curl samples were then rinsed with 40° C. water for 3 minutes. The curl samples were taken out of the rods and air-dried.

The length of each of the curled swatches was measured and an average taken.

| Formula | Average Curl Length (cm) |
|---|---|
| Waving Composition Formula 8A | 8.24 |
| Waving Composition Formula 8B | 7.84 |
| Waving Composition Formula 8C | 7.60 |
| Waving Composition Formula 8D | 8.02 |
| Waving Composition Formula 8E | 7.54 |
| Waving Composition Formula 8F | 8.50 |
| Comparative Composition 9A | 7.34 |
| Comparative Composition 9B | 7.68 |

The results show that curl samples treated with the inventive waving compositions containing ascorbic acid or a derivative thereof achieved comparable curl to those treated with the comparative compositions without ascorbic acid or a derivative thereof.

Example 11

The inventive waving compositions of Example 8 Formulas 8A and 8D and the comparative compositions of Example 9 were evaluated and compared for color change using 6 colored hair swatches as described in Example 10. The results are reported below.

| Formula | Average ΔE |
|---|---|
| Waving Composition Formula 8A | 12.28 |
| Waving Composition Formula 8D | 18.43 |
| Comparative Composition 9A | 15.15 |
| Comparative Composition 9B | 21.08 |

The results show that swatches treated with the inventive waving compositions containing ascorbic acid or a derivative thereof retained significantly more color compared to swatches treated with the comparative compositions without ascorbic acid or a derivative thereof.

Example 12

Waving compositions of the present invention with 0.5%, 1.0%, 2.0%, or 4.0% of ascorbic acid were made having the following formulas using the same procedure described in Example 1.

| | AMOUNT (Wt %) | | | |
|---|---|---|---|---|
| INGREDIENT | Formula 12A | Formula 12B | Formula 12C | Formula 12D |
| Ascorbic Acid | 0.5 | 1.0 | 2.0 | 4.0 |
| Ammonium Bisulfite | 10.0 | 10.0 | 10.0 | 10.0 |
| Pentasodium Pentetate | 0.16 | 0.16 | 0.16 | 0.16 |
| Ammonium Sulfate | 1.2 | 1.2 | 1.2 | 1.2 |
| Cocamidopropyl betaine | 1.75 | 1.75 | 1.75 | 1.75 |
| Isopropanol | 2.0 | 2.0 | 2.0 | 2.0 |
| Monoethanolamine | Adjust pH to 7.0 | Adjust pH to 7.0 | Adjust pH to 7.0 | Adjust pH to 7.0 |
| Deionized Water | QS to 100 | QS to 100 | QS to 100 | QS to 100 |

Compositions of Formulas 12A-12D were evaluated and compared for color change and curl strength as described in Example 10.

| Formula | Average ΔE | Curl Length (cm) |
|---|---|---|
| Waving Composition Formula 12A | 15.29 | 7.78 |
| Waving Composition Formula 12B | 15.01 | 7.68 |
| Waving Composition Formula 12C | 15.35 | 8.20 |
| Waving Composition Formula 12D | 14.89 | 8.16 |

The results show no significant differences in color change between swatches treated with the inventive waving compositions containing ascorbic acid from 0.5% to 4.0%. However, visual inspection showed that yellow tones increased as the percentage of ascorbic acid decreased. An increase in ascorbic acid from 0.5% to 4.0% had no effect on curl strength either statistically or visually. As the percentage of ascorbic acid increased from 0.5% to 2.0% the swatches became smoother. There was no difference in smoothness between the 2.0% and 4.0% ascorbic acid formulas.

Example 13

Waving compositions of the present invention with 0.1, 0.3%, and 0.5% of ascorbic acid were made having the following formulas using the same procedure described in Example 8.

| | AMOUNT (Wt %) | | |
|---|---|---|---|
| INGREDIENT | Formula 13A | Formula 13B | Formula 13C |
| Ascorbic Acid | 0.1 | 0.3 | 0.5 |
| Ammonium Bisulfite | 6.0 | 6.0 | 6.0 |
| Pentasodium Pentetate | 0.16 | 0.16 | 0.16 |
| Ammonium Sulfate | 1.2 | 1.2 | 1.2 |
| Cocamidopropyl betaine | 1.75 | 1.75 | 1.75 |
| Isopropanol | 2.0 | 2.0 | 2.0 |
| Monoethanolamine | Adjust pH to 7.0 | Adjust pH to 7.0 | Adjust pH to 7.0 |
| Deionized Water | QS to 100 | QS to 100 | QS to 100 |

Compositions of Formulas 13A-13C were evaluated for color change (6 swatches) as described in Example 10 and for smoothness (5 swatches). The results are reported below.

| Formula | Average ΔL | Average Δa | Average Δb | Average ΔE |
|---|---|---|---|---|
| Waving Composition Formula 13A | 20.22 | 4.21 | 10.68 | 23.27 |
| Waving Composition Formula 13B | 16.38 | −3.04 | 9.16 | 19.02 |
| Waving Composition Formula 13C | 16.48 | 3.01 | 8.87 | 18.96 |

The results show a visual and statistically significant increase in color retention for swatches treated with the formulas containing 0.3% and 0.5% of ascorbic acid as compared to swatches treated with the formula containing 0.1% of ascorbic acid. Swatches treated with the formula containing 0.1% of ascorbic acid appeared duller than those treated with the formulas containing 0.3% and 0.5% of ascorbic acid. No noticeable difference in smoothness was observed between formulas. Thus, for purposes of the present invention, the term "about 0.3" is intended to exclude 0.1, but embraces, in addition to 0.3 and higher amounts, any amount lower than 0.3% that results in a statistically significant improvement in color retention compared to a same formulation that contains 0.1% ascorbic acid (and thus may include, for example, amounts of ascorbic acid of 0.25, 0.26, 0.27, 0.28 and 0.29).

Example 14

Waving compositions of the present invention with 2.0% of ascorbic acid or ascorbyl glucoside were made having the following formulas using the same procedure described in Example 8.

| INGREDIENT | AMOUNT (Wt %) | |
|---|---|---|
| | Formula 14A | Formula 14B |
| Ascorbic Acid | 2.0 | — |
| Ascorbyl Glucoside | — | 2.0 |
| Ammonium Bisulfite | 6.0 | 6.0 |
| Pentasodium Pentetate | 0.16 | 0.16 |
| Ammonium Sulfate | 1.2 | 1.2 |
| Cocamidopropyl betaine | 1.75 | 1.75 |
| Isopropanol | 2.0 | 2.0 |
| Monoethanolamine | Adjust pH to 7.0 | Adjust pH to 7.0 |
| Deionized Water | QS to 100 | QS to 100 |

The inventive waving compositions of Formulas 14A and 14B and a comparative commercial waving composition containing ammonium thioglycolate were each evaluated for color change as described in Example 10 on swatches colored with 4 different commercially available hair colors. The swatches were colored as described in Example 3 with one of the following artificial hair colors: Color Fusion™ VR (Redken, (New York, N.Y.)), Color Fusion™ 3RV, SOCOLOR™ 4M (Matrix (Clark, N.J.)), and Logics™ 6G (Matrix (Clark, N.J.)). The results are reported below.

| Color | Average ΔE | | |
|---|---|---|---|
| | Formula 14A | Formula 14B | Thioglycolate Waving Composition |
| Color Fusion ™ 5VR | 16.26 | 16.37 | 30.74 |
| Color Fusion ™ 3RV | 12.21 | 12.87 | 13.41 |
| SOCOLOR ™ 4M | 4.15 | 6.71 | 9.40 |
| LOGICS ™ 6G | 6.52 | 6.86 | 15.32 |

The results show that for all color treatments, the swatches treated with the inventive compositions containing ascorbic acid or ascorbyl glucoside retained statistically significantly more color than those swatches treated with a commercially available waving composition containing thioglycolic acid. There was no statistically significant difference in color change between the ascorbic acid formula and the ascorbyl glucoside formula for any of the color treatments. Swatches treated with the commercial composition were roughest to the touch and there was no noticeable difference in roughness between the two inventive compositions.

Example 15

Waving compositions of the present invention with 0%, 0.5%, 1.0%, or 2.0% amodimethicone were made having the following formulas using the same procedure described in Example 8.

| INGREDIENT | AMOUNT (Wt %) | | | |
|---|---|---|---|---|
| | Formula 15A | Formula 15B | Formula 15C | Formula 15D |
| Ascorbic Acid | 2.0 | 2.0 | 2.0 | 2.0 |
| Ammonium Bisulfite | 10.0 | 10.0 | 10.0 | 10.0 |
| Pentasodium Pentetate | 0.16 | 0.16 | 0.16 | 0.16 |
| Ammonium Sulfate | 1.2 | 1.2 | 1.2 | 1.2 |
| Cocamidopropyl betaine | 1.75 | 1.75 | 1.75 | 1.75 |
| Isopropanol | 2.0 | 2.0 | 2.0 | 2.0 |
| Amodimethicone | — | 0.5 | 1.0 | 2.0 |
| Monoethanolamine | Adjust pH to 7.0 | Adjust pH to 7.0 | Adjust pH to 7.0 | Adjust pH to 7.0 |
| Deionized Water | QS to 100 | QS to 100 | QS to 100 | QS to 100 |

The amodimethicone was provided as part of the composition Wacker-Belsil ADM Log 1® (Wacker Chemie AG (Munich, Germany)), which consists of amodimethicone at 15%, Glycerin at 3.5%, Trideceth-5 at 6% and Trideceth-10 at 1.5%.

The inventive waving compositions were evaluated and compared for color change as described in Example 10. The results are reported below.

| Formula | Average ΔE |
|---|---|
| Waving Composition Formula 15A | 16.26 |
| Waving Composition Formula 15B | 13.41 |
| Waving Composition Formula 15C | 13.52 |
| Waving Composition Formula 15D | 12.85 |

The results show that both visually and quantitatively, the presence of the silicone significantly increased color retention. There was also a visual difference in color between the different percentages of silicone. Visually, swatches treated with the 0.5% silicone formula retained less color, while 1.0% and 2.0% performed the same. No significant difference in curl lengths were observed with an increase of the silicone from 0% to 2%. It was also determined that the presence of silicone gave the swatches a smoother feel. It was further determined that the 0.5% silicone formula resulted in slightly rougher swatches as compared to the 1% and 2% silicone formulas, but that the 1% and 2% silicone formulas produced the same roughness.

Example 16

Waving compositions of the present invention with the following formulas were made using the same procedure described in Example 8.

| INGREDIENT | AMOUNT (Wt %) | |
|---|---|---|
| | Formula 16A | Formula 16B |
| Ascorbic Acid | 0.1 | 0.5 |
| Ammonium Bisulfite | 6.0 | 6.0 |
| Pentasodium Pentetate | 0.16 | 0.16 |
| Ammonium Sulfate | 1.2 | 1.2 |
| Cocamidopropyl betaine | 1.75 | 1.75 |
| Isopropanol | 2.0 | 2.0 |
| Amodimethicone | 1.0 | 1.0 |

-continued

| INGREDIENT | AMOUNT (Wt %) | |
|---|---|---|
| | Formula 16A | Formula 16B |
| Monoethanolamine | Adjust pH to 7.0 | Adjust pH to 7.0 |
| Deionized Water | QS to 100 | QS to 100 |

The amodimethicone was provided as part of the composition Wacker-Belsil ADM Log 1®.

The inventive waving compositions were evaluated and compared for color change as described in Example 10. The results are reported below.

| Formula | Average ΔE |
|---|---|
| Waving Composition Formula 16A | 16.21 |
| Waving Composition Formula 16B | 15.11 |

The results show that swatches treated with the formula containing 0.1% ascorbic acid exhibited greater fading compared to those treated with the formula containing 0.5% ascorbic acid. It was observed that the swatches treated with the 0.1% ascorbic acid formula were duller and that the color was less vibrant. The visual observations were confirmed by the quantitative analysis obtained from the colorimeter.

Example 17

A waving composition of the present invention with 4% ascorbic acid and a comparative composition without ascorbic acid were made having the following formulas using the same procedure described in Example 8.

| INGREDIENT | AMOUNT (Wt %) | |
|---|---|---|
| | Formula 17A | Formula 17B |
| Ascorbic Acid | — | 4.0 |
| Ammonium Bisulfite | 14.0 | 14.0 |
| Pentasodium Pentetate | 0.16 | 0.16 |
| Ammonium Sulfate | 1.2 | 1.2 |
| Cocamidopropyl betaine | 1.75 | 1.75 |
| Isopropanol | 2.0 | 2.0 |
| Monoethanolamine | Adjust pH | Adjust pH |
| Deionized Water | QS to 100 | QS to 100 |

Compositions of Formulas 17A and 17B were made in varying pH from 5.5 to 8.5 and evaluated and compared for color change (2 swatches) as described in Example 10. The results are reported below.

| pH | Average ΔE | |
|---|---|---|
| | Formula 17A | Formula 17B |
| 5.5 | 39.10 | 36.69 |
| 6.5 | 23.20 | 18.34 |
| 7.0 | 17.31 | 9.86 |
| 7.5 | 3.56 | 2.77 |
| 8.0 | 4.28 | 3.07 |
| 8.5 | 4.68 | 3.69 |

The composition of Formula 17B was also evaluated for curl strength (5 swatches) as described in Example 10. The results are reported below.

| pH | Average Curl Diameter (cm) | Average Curl Length (cm) |
|---|---|---|
| 5.5 | 1.20 | 3.43 |
| 6.5 | 1.37 | 5.43 |
| 7.0 | 1.73 | 6.17 |
| 7.5 | 1.93 | 7.27 |
| 8.0 | 1.93 | 7.20 |
| 8.5 | 2.73 | 7.27 |

The results show that less color fading occurred as pH increased, but curl became more elongated and looser. The effect of the ascorbic acid in protecting from color fading was significant in the pH range from 5.5 to 7.0. A pH range of from 7.0 to 8.0 gave an acceptable, even curl with a minimal color loss.

Example 18

The waving compositions of Formulas 17A and 17B were also evaluated for color change as described in Example 10 both with and without application of heat during treatment with the waving compositions at various pH. Those swatches that received heat treatment were immersed in the appropriate waving composition and placed in an oven at 50° C. for 25 minutes before continuing with rinsing and neutralizing as describe in Example 3. The results are reported below.

| | Average ΔE | | | |
|---|---|---|---|---|
| | Formula 17A | | Formula 17B | |
| pH | No Heat | Heat | No Heat | Heat |
| 6.5 | 34.402756 | 36.421553 | 31.91549 | 36.581642 |
| 7.0 | 18.574114 | 25.940957 | 15.321109 | 27.721608 |
| 7.5 | 8.5959919 | 18.668117 | 7.8025787 | 15.048088 |
| 8.0 | 3.2044632 | 9.740761 | 5.21081 | 9.6709729 |

The results show that more color fading occurred, but better curl was created with the use of heat across the pH range studied. The effect of ascorbic acid in preventing color loss was significant without the use of heat at pHs up to 7.0. The effect of ascorbic acid in preventing color loss was significant with the use heat at a pH of 7.5.

Example 19

A waving composition of the present invention with 4% of ascorbic acid and a comparative composition without ascorbic acid, were made having the following formulas using the same procedure described in Example 1.

| INGREDIENT | AMOUNT (Wt %) | |
|---|---|---|
| | Formula 19A | Formula 19B |
| Ascorbic Acid | — | 4.0 |
| Ammonium Bisulfite | 10.0 | 10.0 |
| Pentasodium Pentetate | 0.16 | 0.16 |
| Ammonium Sulfate | 1.2 | 1.2 |
| Cocamidopropyl betaine | 1.75 | 1.75 |
| Isopropanol | 2.0 | 2.0 |
| Monoethanolamine | Adjust pH to 7.5 | Adjust pH to 7.5 |
| Deionized Water | QS to 100 | QS to 100 |

The inventive waving composition of Formula 19B and the comparative composition of Formula 19A were each evaluated for color change with heat as described in Example 18 on swatches colored with 3 different commercially available hair colors. The swatches were colored as described in Example 3 with one of the following artificial hair colors: 4N (Matrix (Clark, N.J.)), Logics™ 6NA (Matrix (Clark, N.J.)), and Logics™ 6NA. The results are reported below.

| Color | Average ΔE | |
|---|---|---|
| | Formula 19A | Formula 19B |
| SOCOLOR™ 4N | 34.84 | 30.73 |
| Logics ™ 6NA | 17.20 | 12.55 |
| Logics ™ 6R | 54.94 | 50.21 |

The results show that with heat treatment, ascorbic acid produced a statistically significant reduction in color fading on all three types of colored swatches.

Example 20

The inventive waving composition of Formula 19B and the comparative composition of Formula 19A were each evaluated for color change with heat as described in Example 18, on hair swatches that were shampooed prior to treatment with the waving composition. The swatches were colored as described in Example 10 and then shampooed 10 times with Hair Cleansing Shampoo™ (Redken (New York, N.Y.)). The neutralization step was eliminated.

The results showed that color faded upon shampooing and that swatches treated with heat showed more color loss than those treated without heat. A visual analysis showed that, both with and without the use of heat, the effect of ascorbic acid in protecting hair from color loss was noticeable on shampooed hair.

Example 21

Waving compositions of the present invention and a comparative composition without ascorbic acid or silicone were made having the following formulas using the same procedure described in Example 8.

| INGREDIENT | AMOUNT (Wt %) | | |
|---|---|---|---|
| | Formula 21A | Formula 21B | Formula 21C |
| Ascorbic Acid | 2.0 | 2.0 | — |
| Ammonium Bisulfite | 6.0 | 6.0 | 6.0 |
| Pentasodium Pentetate | 0.16 | 0.16 | 0.16 |
| Ammonium Sulfate | 1.2 | 1.2 | 1.2 |
| Cocamidopropyl betaine | 1.75 | 1.75 | 1.75 |
| Isopropanol | 2.0 | 2.0 | 2.0 |
| Amodimethicone | — | 1.0 | — |
| Monoethanolamine | Adjust pH to 7.0 | Adjust pH to 7.0 | Adjust pH to 7.0 |
| Deionized Water | QS to 100 | QS to 100 | QS to 100 |

The amodimethicone was provided as part of the composition Wacker-Belsil ADM Log 1®.

The inventive waving compositions and comparative composition were evaluated and compared for color change (2 swatches) and curl strength (5 swatches) as described in Example 3. The swatches were then shampooed 15 times with Hair Cleansing Shampoo™ (Redken (New York, N.Y.)). Color change and curl strength were again evaluated. The results are reported below.

| Formula | Average ΔE | |
|---|---|---|
| | Initial | After Shampooing |
| Waving Composition Formula 21A | 13.4 | 16.2 |
| Waving Composition Formula 21B | 11.8 | 15.7 |
| Comparative Composition Formula 21C | 16.8 | 18.5 |

The results show that both ascorbic acid alone and ascorbic acid and silicone reduced color fading initially and after 15 shampoos. No difference was detected in curl strength. Swatches treated with ascorbic acid and silicone were the smoothest, swatches treated with ascorbic acid alone were the second smoothest, and swatches treated with the comparative composition without ascorbic acid or silicone were the roughest after 15 shampoos.

All publications cited in the specification, both patent publications and non-patent publications, are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A waving composition for waving of a keratinous fiber, comprising:
   a) a bisulfite compound, which is present in an amount of from about 6% to about 14% by weight, based on the total weight of the composition;

b) a sulfate compound or urea, wherein the sulfate compound is present in an amount of from about 1.0% to about 2.0% by weight, based on the total weight of the composition, and wherein the urea is present in an amount of from about 2.0% to about 3.0% by weight, based on the total weight of the composition; and c) a lactone comprising δ-gluconolactone which is present in an amount of from about 0.5% to about 4.0%, by weight, based on the total weight of the composition, based on the total weight of the composition.

2. A composition according to claim 1, wherein the bisulfite compound is ammonium bisulfite.

3. A composition according to claim 1, wherein the sulfate compound is ammonium sulfate.

4. A composition according to claim 1, wherein the pH of the composition is from about 5 to about 8.

5. A composition according to claim 1, comprising ammonium bisulfite, ammonium sulfate or urea, and δ-gluconolactone.

6. A composition according to claim 1, further comprising a surfactant, a chelating agent, a swelling agent or penetration enhancer, a pH adjuster, and water.

7. A composition according to claim 6, wherein said surfactant is cocamidopropyl betaine.

8. A composition according to claim 6, wherein said chelating agent is pentasodium pentetate.

9. A composition according to claim 6, wherein said swelling agent or penetration enhancer is isopropanol.

10. A composition according to claim 6, wherein said pH adjuster is monoethanolamine.

11. A composition according to claim 5, further comprising a surfactant, a chelating agent, a swelling agent or penetration enhancer, a pH adjuster, and water.

12. A method for waving a keratinous fiber comprising applying to a keratinous fiber a waving composition comprising:
   a) a reducing agent consisting of a bisulfite compound, which is present in an amount of from about 6% to about 14% by weight, based on the total weight of the composition;
   b) a sulfate compound or urea, wherein the sulfate compound is present in an amount of from about 1.0% to about 2.0% by weight, based on the total weight of the composition, and wherein the urea is present in an amount of from about 2.0% to about 3.0% by weight, based on the total weight of the composition; and
   c) a lactone comprising δ-gluconolactone which is present in an amount of from about 0.5% to about 4.0%, by weight, based on the total weight of the composition, or from about 0.3% to about 4%, by weight, of ascorbic acid or a derivative thereof, based on the total weight of the composition, wherein the keratinous fiber is not treated with any thioglycolate compound or composition.

13. A method according to claim 12, wherein the waving composition has a pH from about 5 to about 8.

14. A method according to claim 12, further comprising applying a neutralizer composition to the keratinous fiber after applying the waving composition to the keratinous fiber.

15. A multi-unit cosmetic kit for treating a keratinous fiber comprising:
   a) a first unit containing a first composition comprising a bisulfite compound and a sulfate compound or urea, and
   b) a second unit containing a second composition comprising a lactone comprising δ-gluconolactone; wherein upon mixing the first and second compositions together to form a waving composition, the bisulfite compound is present in an amount of from 6% to 14% by weight, the sulfate compound is present in an amount of from about 1.0% to about 2.0% by weight, or the urea is present in an amount of from about 2.0% to about 3.0% by weight, and the lactone is present in an amount of from about 0.5% to about 4.0%, by weight, all weights based on the total weight of the waving composition.

16. A kit according to claim 15, further comprising: c) a third unit containing a neutralizer composition.

17. A method of making a waving composition for waving of a keratinous fiber comprising mixing together:
   a) a bisulfite compound, which is present in an amount of from 6% to 14% by weight, based on the total weight of the composition;
   b) a sulfate compound or urea, wherein the sulfate compound is present in an amount of from about 1.0% to about 2.0% by weight, based on the total weight of the composition, and wherein the urea is present in an amount of from about 2.0% to about 3.0% by weight, based on the total weight of the composition; and
   c) a lactone comprising δ-gluconolactone which is present in an amount of from about 0.5% to about 4.0%, by weight, based on the total weight of the composition, based on the total weight of the composition.

18. A composition according to claim 1, further comprising amodimethicone.

19. A composition according to claim 18, wherein the amodimethicone is present in an amount of 0.5% to about 2% by weight, based on the total weight of the composition.

20. A composition according to claim 19, wherein the waving composition has a pH from about 5 to about 8.

* * * * *